(12) United States Patent
Steffens et al.

(10) Patent No.: US 9,376,377 B2
(45) Date of Patent: Jun. 28, 2016

(54) METHOD FOR PRODUCING ISOCYANATES

(71) Applicant: Covestro Deutschland AG, Leverkusen (DE)

(72) Inventors: Friedhelm Steffens, Leverkusen (DE); Jan Busch, Dusseldorf (DE); Markus Hollaus, Bedburg (DE)

(73) Assignee: Covestro Deutschland AG, Kaiser-Wilhelm-Allee, Leverkusen (DE)

( * ) Notice: Subject to any disclaimer, the term of this patent is extended or adjusted under 35 U.S.C. 154(b) by 0 days.

(21) Appl. No.: 14/905,026

(22) PCT Filed: Jul. 21, 2014

(86) PCT No.: PCT/EP2014/065577
§ 371 (c)(1),
(2) Date: Jan. 14, 2016

(87) PCT Pub. No.: WO2015/011070
PCT Pub. Date: Jan. 29, 2015

(65) Prior Publication Data
US 2016/0152558 A1    Jun. 2, 2016

(30) Foreign Application Priority Data
Jul. 26, 2013 (EP) ..................................... 13178270

(51) Int. Cl.
*C07C 263/00* (2006.01)
*C07C 263/10* (2006.01)

(52) U.S. Cl.
CPC ................... *C07C 263/10* (2013.01)

(58) Field of Classification Search
CPC ................................... C07C 263/10

USPC ........................................................ 560/347
See application file for complete search history.

(56) References Cited

U.S. PATENT DOCUMENTS 4,847,408 A    7/1989  Frosch et al.
5,633,396 A    5/1997  Bischof et al.
(Continued)

FOREIGN PATENT DOCUMENTS

EP           1403248 A1 *  3/2004
WO           2011113737     9/2011

*Primary Examiner* — Deborah D Carr
(74) *Attorney, Agent, or Firm* — Donald R. Palladino

(57) ABSTRACT

The invention relates to a method for producing an isocyanate by reacting the corresponding primary amine with phosgene in a reactor (100) which comprises at least one reaction zone (110) and a quenching zone (120) arranged below said reaction zone, having the following steps: (i) introducing a gaseous amine flow (1) and a gaseous phosgene flow (2) into the reactor (100) and reacting the flows in the reaction zone (110) into a product gas flow (3) comprising isocyanate and hydrogen chloride and optionally excess phosgene; (ii) introducing the product gas flow (3) into the quenching zone (120), in which the product gas flow is cooled by injecting a quenching liquid (4) via at least one quenching nozzle (200) such that a liquid flow (5) comprising the quenching liquid (4) and isocyanate and a gaseous flow (6) comprising hydrogen chloride and optionally phosgene are obtained; and (iii) separating the isocyanate from the liquid flow (5) obtained in step (ii); wherein the temperature $T_w^*$, of the wall of the reaction zone (110) directly above the quenching zone (120) is kept at a value which lies maximally 4.0%, preferably maximally 2.0%, below the maximum temperature, $T_w^{max}$, of the wall of the reaction zone, said maximum temperature being specified in Kelvin.

9 Claims, 6 Drawing Sheets

(56) References Cited

U.S. PATENT DOCUMENTS

| | | |
|---|---|---|
| 6,706,913 B2 | 3/2004 | Leimkuhler et al. |
| 6,800,781 B2 | 10/2004 | Herold et al. |
| 6,803,482 B2 | 10/2004 | Jenne et al. |
| 6,838,578 B2 | 1/2005 | Leimkuhler et al. |
| 6,930,199 B2 | 8/2005 | Meyn et al. |
| 6,974,880 B2 | 12/2005 | Biskup et al. |
| 7,084,297 B2 | 8/2006 | Woelfert et al. |
| 7,118,653 B2 | 10/2006 | Brady et al. |
| 7,488,842 B2 | 2/2009 | Knoesche et al. |
| 7,504,533 B2 | 3/2009 | Bohm et al. |
| 7,541,487 B2 | 6/2009 | Pohl et al. |
| 7,615,662 B2 | 11/2009 | Pohl et al. |
| 7,754,915 B2 | 7/2010 | Herold et al. |
| 7,915,444 B2 | 3/2011 | Woelfert et al. |
| 8,563,768 B2 | 10/2013 | Bruns et al. |
| 8,692,016 B2 | 4/2014 | Sanders et al. |
| 8,759,568 B2 | 6/2014 | Lehr et al. |
| 8,809,575 B2 | 8/2014 | Knoesche et al. |
| 9,024,057 B2 | 5/2015 | Biskup et al. |
| 2010/0160673 A1 | 6/2010 | Bruns et al. |
| 2011/0301380 A1 | 12/2011 | Knoesche et al. |

\* cited by examiner

METHOD FOR PRODUCING ISOCYANATES

CROSS-REFERENCE TO RELATED APPLICATIONS

This Application is a National Phase Application of PCT/EP2014/065577, filed Jul. 21, 2014, which claims priority to European Application No. 13178270.8, file Jul. 26, 2013, each of which being incorporated herein by reference.

FIELD

The invention relates to a method for producing an isocyanate by reacting the corresponding primary amine with phosgene in a reactor 100 which comprises at least one reaction zone 110 and a quenching zone 120 arranged there beneath, comprising the steps:
(i) introducing a gaseous amine stream 1 and a gaseous phosgene stream 2 into the reactor 100 and reacting the mixture in the reaction zone 110 to form a product gas stream 3 comprising isocyanate and hydrogen chloride and also possibly excess phosgene;
(ii) introducing the product gas stream 3 into the quenching zone 120 in which the product gas stream is cooled by spraying in a quenching liquid 4 via at least one quenching nozzle 200 in such a manner that a liquid stream 5 comprising quenching liquid 4 and isocyanate and also a gaseous stream 6 comprising hydrogen chloride and possibly phosgene are obtained;
(iii) isolating the isocyanate from the liquid stream 5 obtained in step (ii);
in which the temperature of the wall of the reaction zone 110 immediately above the quenching zone 120, $T_W^*$, is maintained at a value which is at most 4.0%, preferably at most 2.0%, below the maximum temperature in Kelvin of the wall of the reaction zone, $T_W^{max}$.

BACKGROUND

The production of diisocyanates by reaction of diamines in the gas phase is described, for example, in EP 0289840 B1. The diisocyanates that are formed in a tubular reactor are thermally unstable at the reaction temperatures of up to 500° C. A rapid cooling of the reaction gases after the phosgenation reaction to temperatures below 150° C. is therefore necessary in order to prevent the formation of unwanted byproducts due to the thermal decomposition of diisocyanate or due to a further reaction. In EP 0289840 B1 or EP 0749 958 B1, for this purpose, the gaseous mixture continuously leaving the reaction space and which contains, inter alia, diisocyanate, phosgene and hydrogen chloride, is introduced into an inert solvent, e.g. dichlorobenzene. It is disadvantageous in this method that the flow rate with which the gas mixture is passed through the solvent bath must be selected to be relatively low, since at excessive velocities, solvent and the compounds dissolved therein would be entrained. In a subsequent step, the liquid compounds would have to be separated off from the gas. A further disadvantage is that, owing to the low flow rate and a low heat transfer term, large solvent vessels must be used in order to achieve the cooling.

In addition, methods are known which, for cooling the reaction gases, use heat exchangers and/or expand the gases in a vacuum (DE 10158160 A1). The disadvantage of heat exchangers is that, because of the poor heat transfer, large exchange surfaces, and therefore large heat exchangers, are required for effective cooling. In addition, deposits of solids on the relatively cold surfaces of the heat exchangers can occur because of side reactions of the gas mixture such as, e.g., decomposition, polymerization or precipitation.

EP 1 761 483 B1 attempts to decrease the residence time between end of reaction and cooling zone by a region having a reduced flow cross section being situated between the reaction zone and the zone in which the reaction termination is effected.

The reaction termination zone (termed "quench") described in the application WO2007/014936 A2 is a region in which the hot product gases are cooled rapidly by spraying in a quenching liquid. Possible quenching liquids mentioned are solvents, isocyanate mixtures and solvent/isocyanate mixtures. Spraying in a quenching liquid for cooling the reaction mixture and selective dissolution of the formed diisocyanate in the solvent, wherein a first separation into a liquid phase and a gas phase having predominantly phosgene and hydrogen chloride as constituents proceeds is mentioned. The two phases are thereafter fed to a corresponding workup. Possibilities for optimization of this method step are not considered.

A further development method for rapid cooling of the gaseous reaction mixture is offered by spraying one or more quenching liquids into the gas mixture continuously flowing from the reaction zone into the downstream quenching zone, as mentioned in WO 2011/003532 A1 and described in more detail in EP 1403 248 B1.

Spraying in quenching liquid using at least two spray nozzles arranged at the intake of the quenching zone is disclosed in EP 1 403 248 B1. In this case, as quenching liquids, organic solvents are suitable, or a mixture of various organic solvents which do not react with the diisocyanate formed, as described in EP 1 403 248 B1. A solution of the diisocyanate formed in a suitable organic solvent can also be employed, which reduces the amount of solvent used. The diameter of the quenching zone can be greater or smaller than the diameter of the reaction zone. The quenching of the reaction gases can proceed in a single stage and in multiple stages. In this document, reference is made to the fact that the method of spraying in the quenching liquid into the hot reaction gas proceeds in such a manner that contact of the reaction gas with the cold wall is avoided. As a result, the formation of deposits is avoided.

This system is optimized in EP 1 935 875 B1 in that, for termination of the reaction, the reaction mixture is conducted out of the reaction space through a cooling section into which liquids are sprayed in such a manner that the direct cooling in the cooling section proceeds in a single stage manner (that is to say giving only one condensation mixture) into two or more series-connected cooling zones. The diisocyanate generated is obtained in this case in a common condensation mixture. This mixture is preferably collected in a liquid collection vessel, arranged beneath the cooling section. This condensation mixture can be discharged for separating off the isocyanate produced or, preferably after cooling has been performed, in part recirculated to one or more cooling zones of the cooling section. A disadvantage of this use of the "crude product mixture" from the gas phase phosgenation can be soiling of described cooler occurring before entry into the quench. Causes thereof can be unwanted byproducts or polymer compounds from the phosgenation reaction. Also reference is made in EP 1935875 B1 to the fact that the nozzle design of the cooling liquid must be selected in such a manner that the hot reaction gas entering into the quench does not contact the relatively cold walls of the cooling zones and to avoid deposits of solids. In addition to the condensation mixture in the collection vessel, downstream of the cooling section, the gas containing at least hydrogen chloride, phosgene, possibly solvent, and the isocyanate produced, is obtained. This gas stream is taken off from the collection vessel and fed to a scrubbing column and is there substantially freed from the isocyanate fractions thereof. Preferably, this scrubbing proceeds in counterflow to the solvent. The wash phase thus obtained, consisting of diisocyanate and for the most part of solvent, is used in a preferred embodiment as quenching liquid of the first cooling zone of the cooling section. The residual gas from the scrubbing column consists substantially of phosgene, hydrogen chloride and solvent. These vapors leave the column overhead, wherein by means of partial condensation, in a preferred embodiment, via two condensers having different coolant temperatures, the solvent fraction is substantially retained and is recirculated to the column as partial condensate. The residual gas obtained thereafter, which substantially consists of phosgene, hydrogen chloride and solvent residues, is subsequently further treated in a manner known per se, as described, e.g., in EP 1 849 767 B1.

In EP 1 935 876 A1, the use of different suitable quenching liquid streams is likewise mentioned. In this case, reference is made to the use as quenching liquid of the scrubbing liquid from the gas scrubbing of the vapors leaving the condensation vessel downstream of the quench. The reaction is carried out here adiabatically. In the examples according to the invention, the reactors are described as correspondingly insulated, in order to avoid as substantially as possible heat losses. In the non-insulated reactor of the example not according to the invention, in the experiment deposits form on the walls, which lead to the termination of the experiment owing to pressure increase.

According to the teaching of EP-A-1 362 847, temperature fluctuations and asymmetries in the temperature distribution lead to the formation of byproducts which lead to deposits and blockages in the gas phase reactor.

EP 2 196 455 A1 also refers to a plurality of cooling zones in the quenching stage. Here, reference is made for the first time to the integrated combination of the cooling zones of a plurality of reactors with a quenching stage. EP 2 196 455 A1 also refers to the fact that neither mixing spaces nor reaction space permit cooling surfaces, which can give rise to condensation with the consequence of deposits.

WO 2010/063665 A1 refers to a possible problem of the quenching variants cited hitherto. If at least a part of quench liquid is taken off from the collecting vessel after the quench, that is to say the diisocyanate crude product solvent mixture, there is the possibility that solids can be present which can block the quench nozzles. Various techniques are described such as, e.g., centrifugation, distilling off the liquid fraction provided for the quench, or filtration. In order to set the temperature of the selected quench stream for the object in question, the stream can be cooled or heated by means of a heat exchanger.

In WO 2010/115908 A2, a certain embodiment of the quench is disclosed. In order to prevent secondary reactions of the reaction gas during or after the quenching stage, the quench nozzles and the arrangement thereof are designed in such a manner that a substantially complete wetting of the wall in the quench region proceeds. The entire reaction mixture is included thereby. Quenching liquids proposed are solvents and also mixtures with isocyanate or crude mixture of the phosgenation reaction, optionally after particle removal. This document discloses that, owing to inadequate wall wetting in the quenching region, condensate can form on cooler wall zones, which, on account of excessively slow drainage, can lead to secondary reactions with solid deposits.

Said descriptions do not consider a fundamental problem in operating the reactor (including the cooling zone ("quench")) in phosgenation in the gas phase. It is observed during operation, with time, solid deposits on the reactor walls where they are no longer wetted with liquid. The origin of the solid is not completely known. Without wishing to be bound by theory, the supposition is expressed that these are higher molecular weight byproducts from the reaction. These deposits occur more intensively in the region of the quench nozzles. There, the deposits can grow so greatly that a marked constriction of the effective free cross section of the reactor occurs and a correspondingly high pressure drop. Finally, it can even occur that the production needs to be ended, namely when the pressure drop is too high, or there is no longer free passage. FIG. 1 illustrates this situation: a product gas stream 3 passes through a reactor 100 and is cooled by a quench liquid 4. The dashed line at the height of the quench nozzle illustrates the boundary between reaction zone and quench zone: the reaction zone is above the quench nozzle and the quench zone is below the quench nozzle. Above the dashed line, along the periphery of the reactor (that is to say before entry into the actual quench zone), formation of deposits 1000 occurs.

SUMMARY

There is therefore a need for a method for producing diisocyanates by reaction of the corresponding diamines with phosgene in the gas phase, in which the soiling of the reactor wall and cooling zone by solids accumulations is as low as possible.

Taking the abovementioned into account, a subject matter of the present invention is a method for producing an isocyanate by reacting the corresponding primary amine with phosgene in a reactor 100 which comprises at least one reaction zone 110 and a quenching zone 120 arranged there beneath, comprising the steps:
(i) introducing a gaseous amine stream 1 and a gaseous phosgene stream 2 into the reactor 100 and reacting the mixture in the reaction zone 110 to form a product gas stream 3 comprising isocyanate and hydrogen chloride and also possibly excess phosgene;
(ii) introducing the product gas stream 3 into the quenching zone 120 in which the product gas stream is cooled by spraying in a quench liquid 4 via at least one quench nozzle 200 in such a manner that a liquid stream 5 comprising quench liquid 4 and isocyanate and also a gaseous stream 6 comprising hydrogen chloride and possibly phosgene are obtained;
(iii) isolating the isocyanate from the liquid stream 5 obtained in step (ii);
in which the temperature of the wall of the reaction zone 110 immediately above the quenching zone 120, $T_W^*$, is maintained at a value which is at most 4.0%, preferably at most 2.0%, below the maximum temperature in Kelvin of the wall of the reaction zone, $T_W^{max}$.

DETAILED DESCRIPTION

The word "a", in the context of this invention, in connection with countable factors, is only to be considered to mean "one" when this is explicitly stated (e.g. by the expression "exactly one". For example, the expression "a reactor" does not exclude the possibility of the presence of a plurality of (series- or parallel-connected) reactors.

Figure 2:
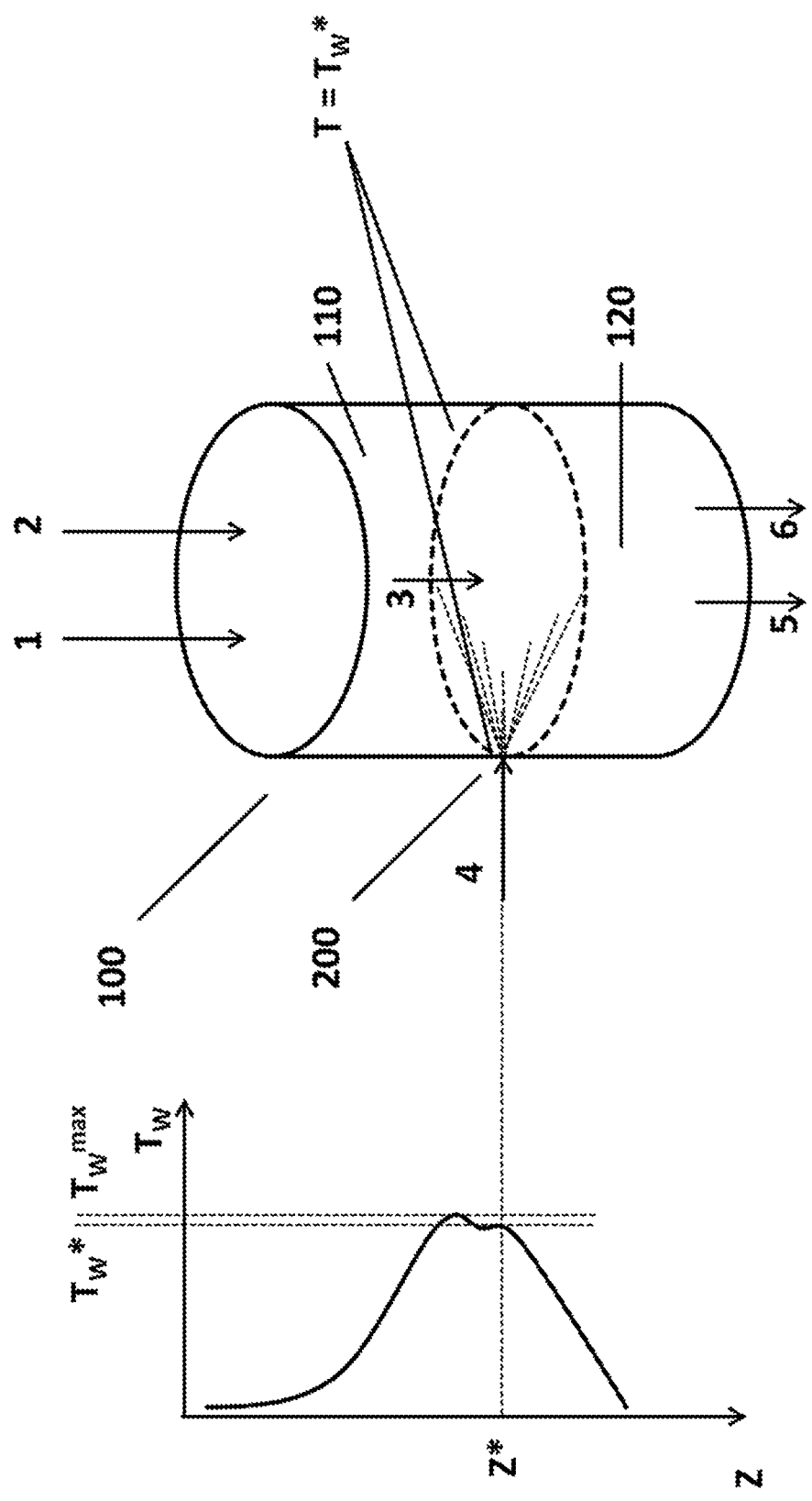
FIG. 2 is a diagrammatic presentation of a gas phase phosgenation reactor and the individual material streams according to embodiments of the present invention.

For further explanation of the terms "$T_W^*$" and "$T_w^{max}$", reference is made to the accompanying drawings:

FIG. 2 on the right-hand side shows diagrammatic presentation of a reactor 100 and the individual material streams. The quench liquid 4 is sprayed into the reactor via a quench nozzle 200 (not shown). For the sake of simplicity, only one stream 4 is shown; preferably, there are a plurality thereof which are arranged around the preferably cylindrical reactor 100 (further details are explained further below). The localization of the first quench nozzle in the direction of flow of the product gas 3 defines the transition between reaction zone 110 and quench zone 120 (indicated in the drawing by a dashed line all around the reactor). On the left-hand side of FIG. 2, the temperature profile of the reactor wall is shown schematically: owing to the exothermic nature of the reaction between 1 and 2, the wall temperature $T_W$ increases first to a maximum value $T_W^{max}$. In the arrangement shown in which the quench liquid 4 is sprayed into the reactor 100 perpendicularly to the direction of flow of the product gas 3, inter alia, also owing to upwards-sprayed quench liquid, there is a temperature drop even above the quench to a value $T_W^*$. In the region beneath the quench nozzle, the temperature falls rapidly owing to the intimate mixing of product gas stream 3 with the quench liquid 4 and also the wetting of the wall with relatively cold quench liquid 4 and relatively cold stream 5.

Figure 3:
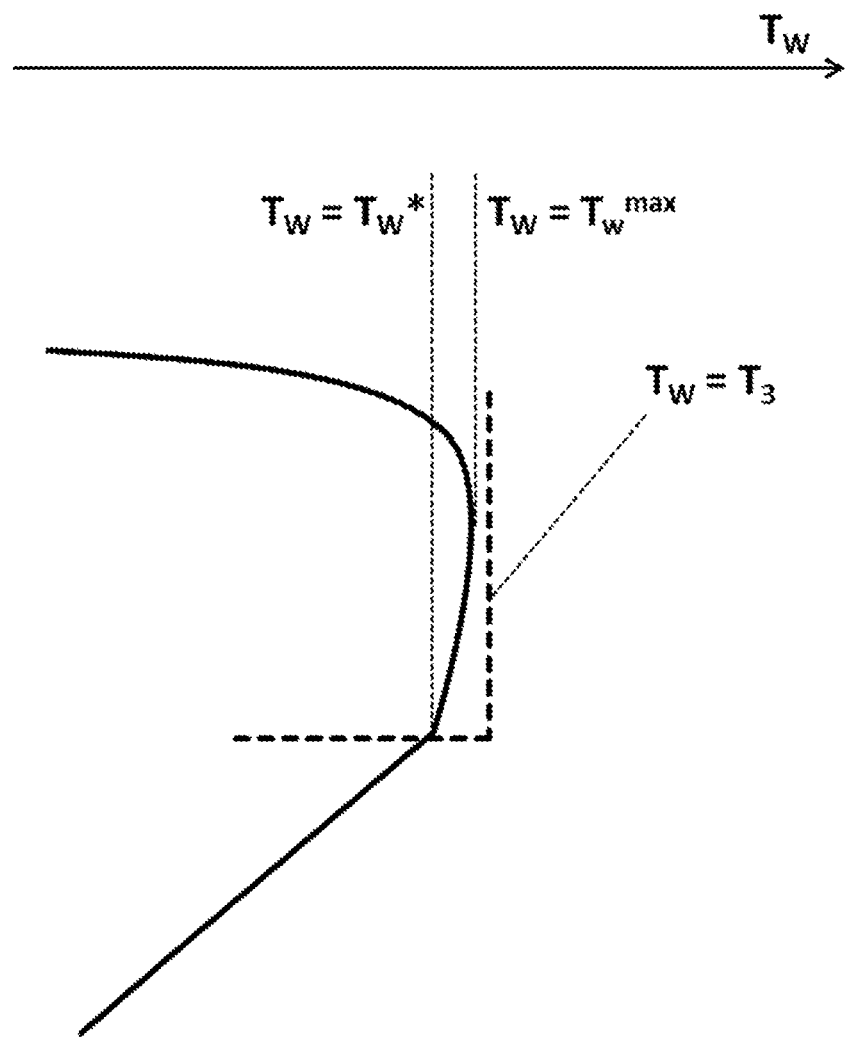
FIG. 3 is a chart illustrating the connection between the individual reactor wall temperatures according to embodiments of the present invention.

FIG. 3, in a detail enlargement, shows the connection between the individual temperatures. According to the invention, it is now essential that $T_W^*$ is at most 4.0%, preferably at most 2.0%, below the maximum temperature in Kelvin of the wall of the reaction zone, $T_w^{max}$. This means that $$100\% \cdot [(T_W^{max}/K)-(T_W^*/K)]/(T_W^{max}/K)$$
must be ≤4.0% (preferably ≤2.0%).

In FIG. 3, likewise the theoretical optimum temperature course is shown by dashes: before entry into the quench, the temperature of the wall of the reactor is equal to the temperature of the product gas 3, $T_3$, on entry into the quench, the temperature of the wall of the reactor decreases abruptly.

For determination of $T_W^{max}$, a plurality of temperature sensors (e.g. surface thermometers) are distributed over the length and periphery of the reactor on the outer wall of the reactor. The number of temperature sensors required is dependent on the size of the reactor. For a person skilled in the art it is easy to determine how many temperature sensors are required for a given reactor size and reactor geometry. $T_W^{max}$ according to the invention is the maximally observed temperature. $T_W^*$ is measured via one or more temperature sensors on the periphery directly above the port of the quench nozzles 200. When a plurality of quench nozzles 200 are present successively arranged in the direction of flow of the product gas stream 3, $T_W$ is measured directly above the first quench nozzles 200 in the direction of flow of the product gas stream 3. Here also, the number of temperature sensors that are required is dependent on the size of the reactor. For a person skilled in the art it is again easy to determine how many temperature sensors are required for a given reactor size and reactor geometry.

The temperatures measured in this manner on the outer wall of the reactor reflect the conditions on the inner wall of the reactor that are actually important with sufficient accuracy, since various factors lead in practice to a negligibly small difference between the temperatures measured as described herein before and those on the inner wall:
  metallic wall materials having good conductivity
  relatively low thickness of the reactor wall
  insulation of the reactor wall from the surroundings Hereinafter, the invention will be described in detail with reference to various embodiments. Here, various embodiments can be combined as desired with one another, provided that the contrary does not clearly result from the context for a person skilled in the art.

Using the present invention, isocyanates that can be vaporized without decomposition can be produced.

Suitable primary amines for carrying out the method according to the invention are those which may be vaporized without decomposition, in particular the isomers of toluylenediamine (hereinafter TDA), the isomers of methylenediphenyldiamine (hereinafter MDA), the isomers of naphthyldiamine (hereinafter NDA), 1,6-hexamethylenediamine (hereinafter HDA), the isomers of isophoronediamine (hereinafter IDPA) and the isomers of diaminodicyclohexylmethane (hereinafter H12-MDA). Where said amines can be present in various isomeric forms, without this being stated, all distributions of isomers are included.

Particular preference is given to TDA. Usually TDA, which is preferably used, comprises 78% by mass to 82% by mass 2,4-TDA and 18% by mass to 22% by mass 2,6-TDA, based on the total mass of the 2,4- and 2,6-TDA isomers. On the basis of the total mass of TDA, the 2,4- and 2,6-TDA isomers preferably account for a total of 95.0% by mass to 100% by mass, particularly preferably from 98.0% by mass to 100% by mass. Preferably, the content of TDA isomers with $NH_2$ groups in the ortho position to one another in the TDA to be used is less than 0.2% by mass, based on the total mass of the TDA to be used. Methods for providing TDA having the said requirements are known to those skilled in the art.

Methods for providing a gaseous amine stream 1 and a gaseous phosgene stream 2 for carrying out step (i) are known in principle to those skilled in the art. Hereinafter, preferred embodiments are described.

Converting the amine into the gas phase can be performed in all evaporation apparatuses known from the prior art. Preferably, evaporation apparatuses are used in which a small working content is conducted with high circulation throughput via a falling-film evaporator and in this case for minimizing the thermal stress of the starting amines, the evaporation operation—as described above—is optionally supported by feeding in inert gas and/or vapors of an inert solvent.

In a preferred embodiment of the method according to the invention, evaporation apparatuses are used in which a small working content is circulated via at least one microheat exchanger or microevaporator. The use of corresponding heat exchangers for evaporating amines is disclosed, e.g., in EP 1 754 698 A2. Preferably, in the method according to the invention, the apparatuses disclosed in paragraphs [0007] to [0008] and [0017] to [0039] of EP 1 754 698 A2 are used.

In addition, the evaporation—and if necessary superheating—of the starting amine preferably proceeds in a multi-stage manner, in order to avoid non-evaporated droplets in the gaseous amine stream 2. Particularly preferably, multistage evaporation and superheating steps, in which demisters are installed between the evaporation and superheating systems and/or the evaporation apparatuses also have the function of a demister. Suitable demisters are known to those skilled in the art. After leaving the last superheater in the direction of flow, the gaseous amine preheated to the preset temperature thereof is fed to the reaction zone 110 for reaction with a mean residence time of preferably 0.01 s to 60 s, very particularly preferably 0.01 s to 30 s, particularly preferably 0.01 s to 15 s. Independently of the design of the feed of amine in detail, the risk of renewed droplet formation is countered by technical measures, e.g. sufficient insulation for avoidance of losses by radiation.

In the method according to the invention, it is advantageous to use phosgene in excess with respect to the amine groups that are to be reacted. In this case, the product gas stream 3 and the gas stream 6 also contain excess phosgene. Preferably, a molar ratio of phosgene to amine groups of 1.1:1 to 20:1, particularly preferably 1.2:1 to 5:1 is present. Also, the phosgene is heated to temperatures of 200° C. to 600° C. and is fed (stream 2) to the reaction zone 110 optionally diluted with an inert gas such as $N_2$, He, Ar, or with the vapors of an inert solvent, e.g. aromatic hydro-carbons without or with halogen substitution such as, e.g., chlorobenzene or o-dichlorobenzene.

The separately heated reactants 1 and 2 are preferably introduced via a nozzle arrangement into the reaction zone 110 of the reactor 100 and preferably are reacted adiabatically there. Adiabatic reaction means that a targeted removal of the resultant heat of reaction by a heat transfer medium is dispensed with. Therefore, the reaction enthalpy—apart from unavoidable heat losses—is quantitatively reflected in the temperature difference between product stream and reagent gas stream. The nozzle arrangement for introducing the reagent gas streams 1 and 2 can be designed in various ways known to those skilled in the art; examples may be found, e.g., in EP 2 199 277 B1, paragraph [0017] to [0019], EP 1 449 826 B1, paragraph [0011] to [0012], EP 1 362 847 B1, paragraph [0011] to [0012], EP 1 526 129 B1, paragraph [0009] to [0011] and EP 1 555 258 B1, paragraph [0008] to [0011].

The reactor 100 preferably has a circularly symmetrical cross section not only in the region of the reaction zone 110, but also in the region of the quench zone 120. In this case, the entire reactor can be cylindrical, as shown in the drawings. However, it is also possible that the cross section changes, as described, e.g., in EP 1275639 B1, paragraph [0009], EP 1275640 A1, paragraph [0014], EP 1 403 248 B1, paragraph [0014] to [0015], EP 193 5876 A1, paragraph [0012] to [0016] and EP 2 196 455 B1, paragraphs [0015] to [0026] and [0027] to [0030]. Further details on the construction of suitable phosgenation reactors are known to those skilled in the art.

In the reaction zone 110, amine 1 and phosgene 2 are reacted rapidly, preferably adiabatically, to give the corresponding isocyanate. The reaction is preferably carried out in such a manner that the amine is completely reacted before entry into the quench zone.

In a preferred embodiment of the method according to the invention, the throughput capacity of the reactor 100 used under the reaction conditions required according to the invention is greater than >1 t of amine/h, preferably 2-50 t of amine/h, particularly preferably 2-12 t of amine/h. Particularly preferably, these values apply to toluylenediamine, 1,6-diaminohexane and isophoronediamine. Throughput capacity in this case is to be taken to mean that in the reactor 100, the said throughput capacity of amine per hour can be reacted.

After the phosgenation reaction in the reaction zone 110 is complete, the gaseous reaction mixture 3, which comprises at least the sought-after isocyanate and hydrogen chloride (and also, in the case of superstoichiometric use of phosgene, also unreacted phosgene), is passed (step (ii)) into the quench zone 120, where the isocyanate formed is substantially condensed by spraying in the quench liquid 4. Possibilities for the structure and operation of the quench zone 120 are known in principle from the prior art. If the requirements according to the invention with respect to temperature $T_W^*$ are maintained, the apparatuses and methods of the prior art can be used. Possible configurations of the quench zone 120 are disclosed, for example, in EP 1 403 248 A1 and EP 1 935 875 A1.

The temperature of the quench liquid 4 is preferably selected in such a manner that it firstly is high enough in order to cleave the carbamoyl chloride corresponding to the isocyanate back into isocyanate and hydrogen chloride (although it is in no way certain whether the carbamoyl chloride intermediate known from the liquid-phase phosgenation is also formed in the gas phase phosgenation, since it is conceivable, independently thereof, that in the quench liquefied isocyanate 5 partially reacts with the hydrogen chloride gas 6 present to form carbamoyl chloride, the temperature of the quench liquid 4 should be high enough in order to suppress this reaction). On the other hand, isocyanate and optionally the solvent co-used in the gaseous amine stream and/or gaseous phosgene stream as diluent should condense or dissolve in the solvent to the greatest extent, whereas excess phosgene, hydrogen chloride and inert gas optionally co-used as diluent pass through the quench zone 120 to the greatest extent in non-condensed or non-dissolved form, in such a manner that the temperature of the quench liquid 4 also must be selected so as to be not too high. For the selective production of isocyanate from the gaseous reaction mixture 3, quench liquids 4 kept at a temperature of 80° C. to 200° C., preferably 80 C to 180° C., are particularly highly suitable. The quench liquid 4 in this case is preferably selected from chlorobenzene, dichlorobenzene, isocyanate and mixtures of the above-mentioned liquids. It is predictable simply to a person skilled in the art, on the basis of physical data at a given temperature, pressure and composition what mass fraction of the isocyanate passes through in the quench condensed, or passes there through non-condensed. Likewise, it is simple to predict what mass fraction of the excess phosgene, hydrogen chloride and inert gas optionally used as diluent passes through the quench non-condensed or dissolves in the quench liquid.

Preferably, the reagent gases and product gases flow through the reactor 100 without substantial backmixing. This is ensured by a pressure drop over the reaction zone 110, preferably over the reaction zone 110 and the subsequent quench zone 120. Preferably, the pressure drop exists between the start of the reaction zone 110 on the one hand and the exit from the quench zone 120 on the other. Preferably, the absolute pressure at the start of the reaction zone 110 is 200 mbar to 3000 mbar, and downstream of the quench zone 120 is 150 mbar to 2500 mbar. However, it is of importance in this case only to maintain a differential pressure over the reaction zone 110, preferably over the reaction zone 110 and the quench zone 120, of preferably at least 50 mbar to ensure the said directed flow and good mixing of the reagents.

In step (ill), the isocyanate is obtained from the liquid mixture 5 which exits from the quench zone 120. This proceeds preferably via workup by distillation, particularly preferably as described in EP 1 371 633 A1.

The gas mixture 6 leaving the quench zone 120 is preferably freed from residual isocyanate possibly present in a downstream gas scrubber using a suitable scrubbing liquid and preferably then freed from excess phosgene in a manner known per se. This can proceed by means of a cold trap, absorption in an inert solvent (e.g. chlorobenzene or dichlorobenzene) or by absorption and hydrolysis on activated carbon. Preferably, this step proceeds as described in WO2011/003532A1; see, in particular, page 11, line 31 to page 25, line 15. Preferably, the excess phosgene separated off from the gas mixture is recirculated to the reactor. The hydrogen chloride gas passing through the phosgene recovery stage can be recycled in a manner known per se for recovery of the chlorine required for the phosgene synthesis. The scrubbing liquid arising after use thereof for gas scrubbing is then preferably at least in part used in the corresponding zone of the reaction space as quench liquid for cooling the gas mixture.

Figure 1:
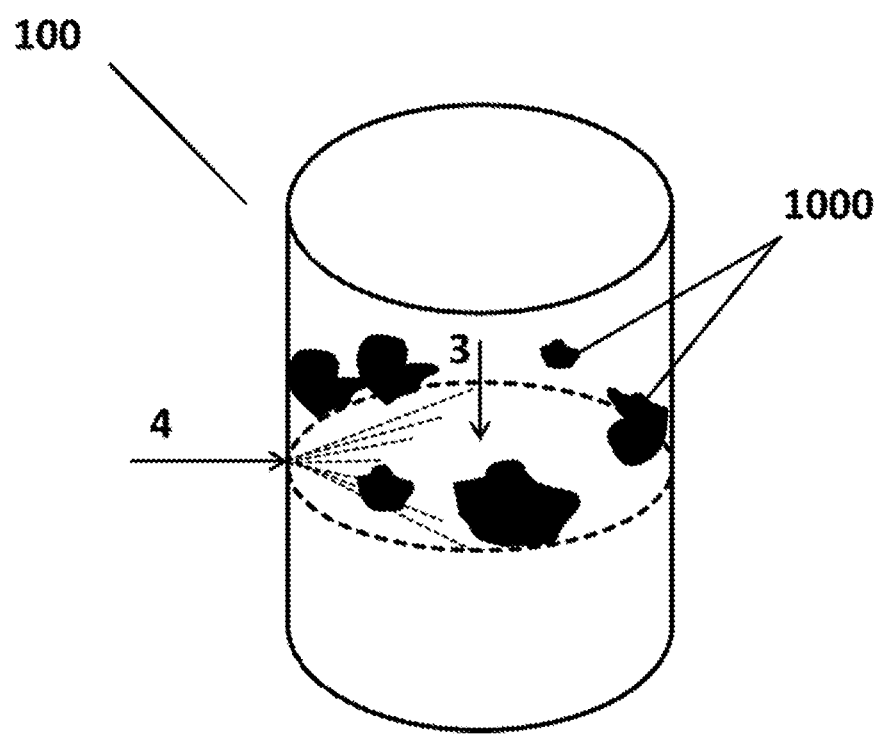
FIG. 1 is an illustration of a gas phase phosgenation reactor having solid deposits on the reactor walls.

It is then essential to the invention that $T_W^*$ is at most 4.0%, preferably at most 2.0%, below the maximum temperature of the inner wall of the reaction zone in Kelvin, $T_w^{max}$. This is because it has been found that deposits 1000 (FIG. 1) occur less, the higher is the temperature of the reactor wall in the region above the quench zone 120.

This can be ensured in various ways which can also be combined with other another:

In a preferred embodiment, the requirements according to the invention of the temperature $T_W^*$ are ensured by at least one of the following measures:
(a) insulation of the reactor wall externally,
(b) heating the reactor wall from the outside,
(c) insulation between wall of the reaction zone and wall of the quenching zone.

Materials and methods for the insulation are known to those skilled in the art. Using measure (a), heat losses to the outside are minimized. In the case of measure (b), the reactor wall is heated, preferably electrically, from the outside above the quench zone 120. In this way, the heat losses are compensated for by heat conduction in the wall. Measure (c) suppresses in this case the heat conduction in the reactor wall, therefore prevents the colder wall temperatures in the quench zone 120 having an effect on the reaction zone 110.

In a further preferred embodiment, the requirements according to the invention of the temperature $T_W^*$ are ensured by at least one of the following measures:
(a) increasing the temperature of the quench liquid,
(b) decreasing the amount of quench liquid sprayed in.

These measures of course cannot be used to any extent desired, since the function of the quench, the rapid cooling of the product gas stream 3, must be retained. A person skilled in the art, from the given boundary conditions of a production plant, can readily determine what minimum flow rate of quench liquid (at a given temperature of the quench liquid) is required or what temperature the quench liquid (for a given mass flow rate) may have as a maximum.

Structure and arrangement of the quench nozzles are preferably as disclosed in EP 1403 248 B1.

Figure 4:
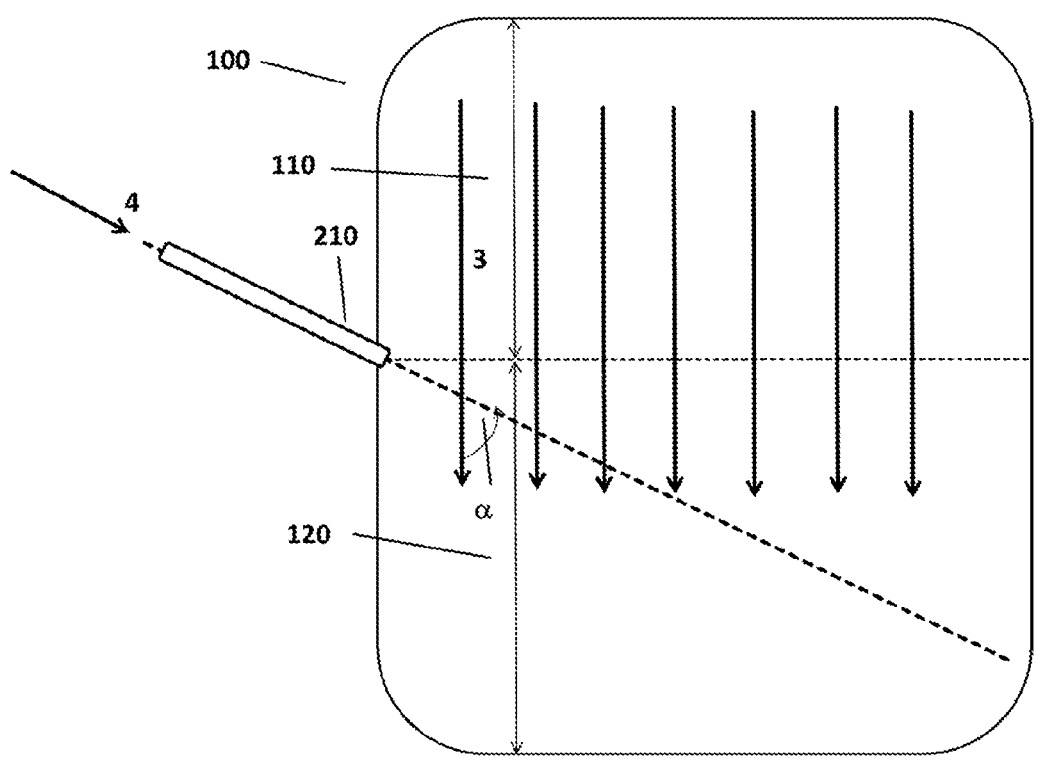
FIGS. 4 and 5 are illustrations of the orientation quench nozzles according to embodiments of the present invention.

In a further preferred embodiment, the quench nozzles 200, when a plurality of quench nozzles are arranged successively in the direction of flow of the product gas stream 3(s) are oriented in such a manner that the linear elongation, at least the first quenching nozzles in the direction of flow of the product gas stream 3 of the nozzle tube/the nozzle tubes 210 is/are at an angle to the direction of flow of the product gas stream 3 of 20° to 80°, preferably from 20° to 50°, (FIG. 4, angle α). The linear elongation of the nozzle tube corresponds in this case to the direction of flow which the quench liquid would have if it were to exit without any spreading as a straight jet from the exit tube of the nozzle (the nozzle tube). By this means it is prevented that quench liquid 4 is spread upwards to the region of the reaction zone 110. This is because if the quench nozzle 200 is arranged at a right angle to the product gas flow 3, some of the quench liquid 4 also always arrives at the inner wall of the reaction zone 110 immediately above the nozzles and there effects an unwanted temperature decrease which can be a cause for formation of deposits. This can be effectively decreased by a corresponding design of the quench. It is critical for this to deflect the direction of spraying of the quench nozzle 200 in the direction of the gas flow 3, that is to say correspondingly to spray downwards (cf. FIG. 4). The quench liquid 4 in this case is sprayed with conventional spray nozzles or through openings, for example slots or holes, preferably as a flat jet, that is to say without spreading in the vertical direction. It was found in operational experiments in a pilot plant, that via a spray angle of 20° to 80°, preferably 20° to 50°, relative to the gas flow 3, an "upwards spraying" and solids accumulation can effectively be prevented. Service life and availability of gas-phase reactors 100 are thereby increased.

Figure 5:
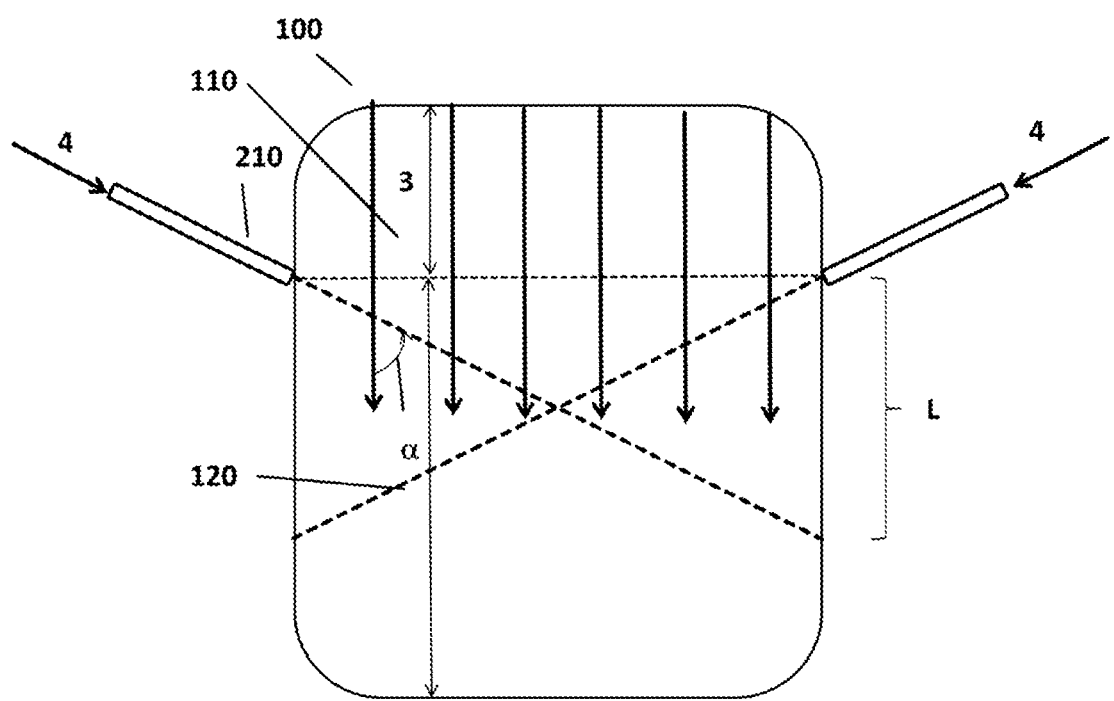

As an alternative to the description of the spray angle, the effect of nozzle geometry can also be described via the distance L which, for a certain quench arrangement, results between the quench plane and the plane on which the quench liquid impacts the reactor wall. Depending on the spreading of the nozzle, this distance is not uniform, and so the following simplified depiction is selected: the distance L is defined as the distance between the quench plane and the theoretical point of intersection of the elongation of the spray direction and the reactor wall according to FIG. 5. The expression quench plane in this case means the theoretical plane through the point at which the exit opening of the first quench nozzle in the direction of flow of the product gas protrudes into the interior of the reactor; this is understood according to the invention as the start of the quench zone. For a given reactor geometry the two dimensions spray-in angle α and distance to the quench plane L may readily be converted into one another by a person skilled in the art. A critical difference between the two measures is that the distance to the quench plane L does not change with changed reactor diameter. It has now been found that for the value L there is a preferred minimum value which—independently of the value of the spray-in angle α—it should preferably not fall beneath. In a further embodiment of the method according to the invention, therefore, the quench nozzles 200, when a plurality of quench nozzles are arranged successively in the direction of flow of the product gas stream 3, at least the first quench nozzles in the direction of flow of the product gas stream 3, are arranged in such a manner that the linear elongation of the nozzle tube crosses the wall of the quenching zone at a point which is beneath the start of the quenching zone by at least the distance L (cf. FIG. 5). The value L according to the invention is 15 cm, preferably 70 cm.

EXAMPLES

Example 1

Figure 6:
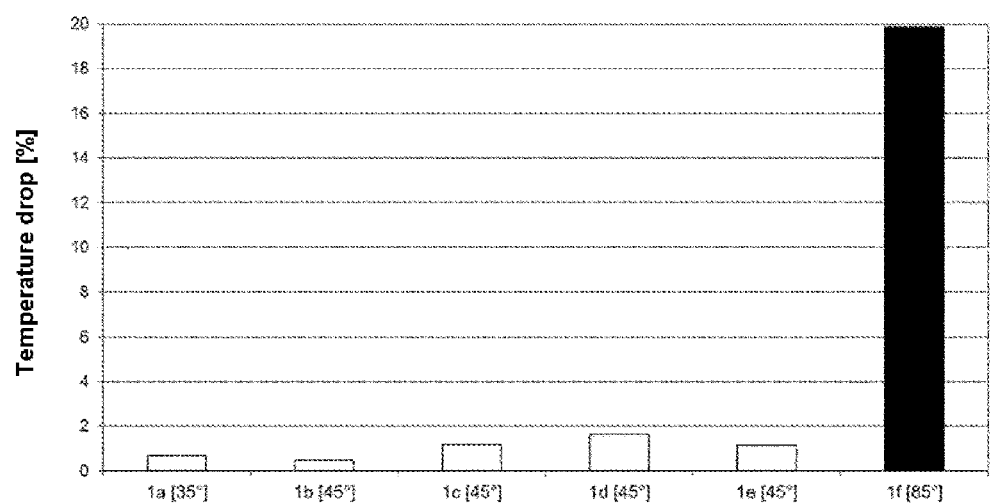
FIG. 6 shows experimental results of a study on the effect of the spraying angle and on the decrease in the wall temperature in the region of quench.

Dependence of the Temperature Profile of the Reactor Wall on the Spray Introduction Angle α or on the Distance L FIG. 6 (FIG. 6) shows experimental results of a study on the effect of the spraying angle α on the decrease in the wall temperature in the region of the quench. The study was carried out in an experimental appliance on a pilot scale for production of toluylene diisocyanate using phosgenation of the associated amine in the gas phase. $T_W^{max}$ in all experiments was between 400 and 500° C. The temperature of the quench liquid was 125° C. The reactor was cylindrical with a constant internal diameter of 800 mm in the reaction zone and quench zone. The percentage decrease in wall temperature in this case is defined as above as $$100\% \cdot [(T_W^{max}/K) - (T_W^*/K)]/(T_W^{max}/K).$$

| | | | Example: | | | |
|---|---|---|---|---|---|---|
| | 1a | 1b | 1c | 1d | 1e | 1f (comparison) |
| α | 35° | 45° | 45° | 45° | 45° | 85° |

The sharp rise in temperature decrease at a spraying direction virtually perpendicular to the direction of flow of the reaction mixture (85°, right-hand bar) may clearly be seen. The experiments with spray angles of 35° and 45° (five bars on the left-hand side), in contrast, only lead to small temperature drops.

FIG. 6 in addition shows the correlation between temperature decrease and increased solids deposition. Black bars show experimental runs with a markedly more severe solids accumulation on the reactor inner wall in the reaction of the quench nozzles in comparison with the other experimental runs. The risk of solids accumulation can therefore be markedly affected by restricting the temperature decrease, here realized through suitable choice of spray angle.

The angles stated in FIG. 6 may be described as follows as a distance between the impact plane of the quench liquid and quench plane:

| Example No. | Spray angle α | Distance L |
|---|---|---|
| 1a | 35° | 114.3 cm |
| 1b-e | 45° | 80.0 cm |
| 1f | 85° | 7.0 cm |

The temperature decrease was therefore reduced markedly by setting a distance L of 80 cm in comparison with 7 cm.

The invention claimed is:

1. A method for producing an isocyanate by reacting the corresponding primary amine with phosgene in a reactor which comprises at least one reaction zone and a quenching zone arranged below the reaction zone, comprising:
    (i) introducing a gaseous amine stream and a gaseous phosgene stream into the reactor and reacting the mixture in the reaction zone to form a product gas stream comprising isocyanate and hydrogen chloride;
    (ii) introducing the product gas stream into the quenching zone in which the product gas stream is cooled by spraying in a quench liquid via at least one quench nozzle in such a manner that a liquid stream comprising quench liquid and isocyanate is obtained; and
    (iii) isolating the isocyanate from the liquid stream obtained in step (ii);
    wherein
    the temperature of the wall of the reaction zone immediately above the quenching zone is maintained at a value which is at most 15% below the maximum temperature in Kelvin of the wall of the reaction zone.

2. The method of claim 1, in which the temperature of the wall of the reaction zone immediately above the quenching zone is held at a value which is at most 2.0% below the maximum temperature in Kelvin.

3. The method of claim 1, in which the requirement of the temperature of the wall of the reaction zone immediately above the quenching zone is achieved by at least one of the following measures:
    (a) insulation of the reactor wall externally,
    (b) heating the reactor wall from the outside, and
    (c) insulation between wall of the reaction zone and wall of the quenching zone.

4. The method of claim 1, in which the requirement of the temperature of the wall of the reaction zone immediately above the quenching zone is achieved by at least one of the following measures:
    (a) increasing the temperature of the quench liquid, and
    (b) decreasing the amount of quench liquid sprayed in.

5. The method of claim 1, in which, when a single quench nozzle is used, the quench nozzle, or, when a plurality of quench nozzles are arranged successively in the direction of flow of the product gas stream, at least the first quench nozzles in the direction of flow of the product gas stream is/are oriented in such a manner that the linear elongation of the nozzle tube/the nozzle tubes is/are at an angle to the direction of flow of the product gas stream of 20° to 80°.

6. The method of claim 1, in which, when a single quench nozzle is used, the quench nozzle, or, when a plurality of quench nozzles are arranged successively in the direction of flow of the product gas stream, at least the first quench nozzles in the direction of flow of the product gas stream is/are orientated in such a manner that the linear elongation of the nozzle tube/the nozzle tubes is/are at an angle to the direction of flow of the product gas stream of 50° to 80°.

7. The method of claim 1, in which, when a single quench nozzle is used, the quench nozzle, or, when a plurality of quench nozzles are arranged successively in the direction of flow of the product gas stream, at least the first quench nozzles in the direction of flow of the product gas stream, is/are orientated in such a manner that the linear elongation of the nozzle tube crosses the wall of the quenching zone at a point which is beneath the start of the quenching zone by at least the distance L, wherein L=15 cm.

8. The method of claim 1, in which, when a single quench nozzle is used, the quench nozzle, or, when a plurality of quench nozzles are arranged successively in the direction of flow of the product gas stream, at least the first quench nozzles in the direction of flow of the product gas stream, is/are orientated in such a manner that the linear elongation of the nozzle tube crosses the wall of the quenching zone at a point which is beneath the start of the quenching zone by at least the distance L, wherein L=70 cm.

9. The method claim 1, in which the primary amine is selected from the group consisting of the isomers of toluylenediamine, the isomers of methylenediphenyldiamine, the isomers of naphthyldiamine, 1,6-hexamethylenediamine, the isomers of isophorenediamine, and the isomers of diaminodicyclohexylmethane.

* * * * *